(12) United States Patent
Hill et al.

(10) Patent No.: US 9,005,523 B2
(45) Date of Patent: Apr. 14, 2015

(54) COLD-MIST DECONTAMINATION UNIT AND METHOD OF OPERATING SAME

(71) Applicant: American Sterilizer Company, Mentor, OH (US)

(72) Inventors: Aaron L. Hill, Madison, OH (US); Thaddeus J. Mielnik, Concord, OH (US)

(73) Assignee: American Sterilizer Company, Mentor, OH (US)

( * ) Notice: Subject to any disclaimer, the term of this patent is extended or adjusted under 35 U.S.C. 154(b) by 177 days.

(21) Appl. No.: 13/779,958

(22) Filed: Feb. 28, 2013

(65) Prior Publication Data

US 2013/0302208 A1     Nov. 14, 2013

Related U.S. Application Data

(60) Provisional application No. 61/645,254, filed on May 10, 2012.

(51) Int. Cl.
| | | |
|---|---|---|
| A61L 9/00 | (2006.01) | |
| G01D 11/26 | (2006.01) | |
| F26B 11/18 | (2006.01) | |
| B67D 5/08 | (2006.01) | |
| A61L 2/24 | (2006.01) | |
| A61L 2/20 | (2006.01) | |
| A61L 2/22 | (2006.01) | |

(52) U.S. Cl.
CPC . *A61L 2/24* (2013.01); *A61L 2/208* (2013.01); *A61L 2/22* (2013.01); *A61L 2202/14* (2013.01)

(58) Field of Classification Search
CPC ........... A61L 2/00; A61L 2/186; A61L 2/208; A61L 9/015; A61L 9/14; B01B 1/00
USPC ........ 34/200; 422/1, 28, 31–33, 50, 105, 119, 422/123, 298, 305–306; 222/1, 52, 325
See application file for complete search history.

(56) References Cited

U.S. PATENT DOCUMENTS

| | | | |
|---|---|---|---|
| 2004/0114129 A1 | 6/2004 | Gogolla et al. | 356/4.01 |
| 2006/0008379 A1 | 1/2006 | Mielnik et al. | 422/32 |
| 2007/0140893 A1 | 6/2007 | McVey et al. | 422/3 |
| 2007/0274858 A1* | 11/2007 | Childers et al. | 422/28 |
| 2008/0065346 A1 | 3/2008 | Shkipin | 702/151 |
| 2009/0047174 A1 | 2/2009 | Hill | 422/28 |

(Continued)

FOREIGN PATENT DOCUMENTS

| | | | | |
|---|---|---|---|---|
| AU | 2012/100211 | 3/2012 | | A61L 9/14 |
| GB | 2223678 | 4/1990 | | A61L 2/24 |

(Continued)

*Primary Examiner* — Monzer R Chorbaji
(74) *Attorney, Agent, or Firm* — Kusner & Jaffe

(57) ABSTRACT

A method of decontaminating a room or space, comprising the steps of providing a cold-mist decontamination device capable of generating an atomized mist comprised of a decontaminant and water, inputting into an internal processor the parameters of the room or space and the concentration of the decontaminant in the decontamination solution, measuring the temperature and humidity in the room or space, and determining the maximum amount of the decontamination solution that can be introduced into the room or space in atomized form without condensing the decontaminant on surfaces within the room or space.

13 Claims, 1 Drawing Sheet

(56) References Cited

U.S. PATENT DOCUMENTS

2010/0316530 A1 12/2010 Morgantini et al. ............ 422/29
2011/0280767 A1 11/2011 Goessens ...................... 422/106

FOREIGN PATENT DOCUMENTS

| WO | WO2011/099935 | 8/2011 | ................ A61L 2/20 |
| WO | WO2011/157812 | 12/2011 | .............. C02F 1/467 |

* cited by examiner

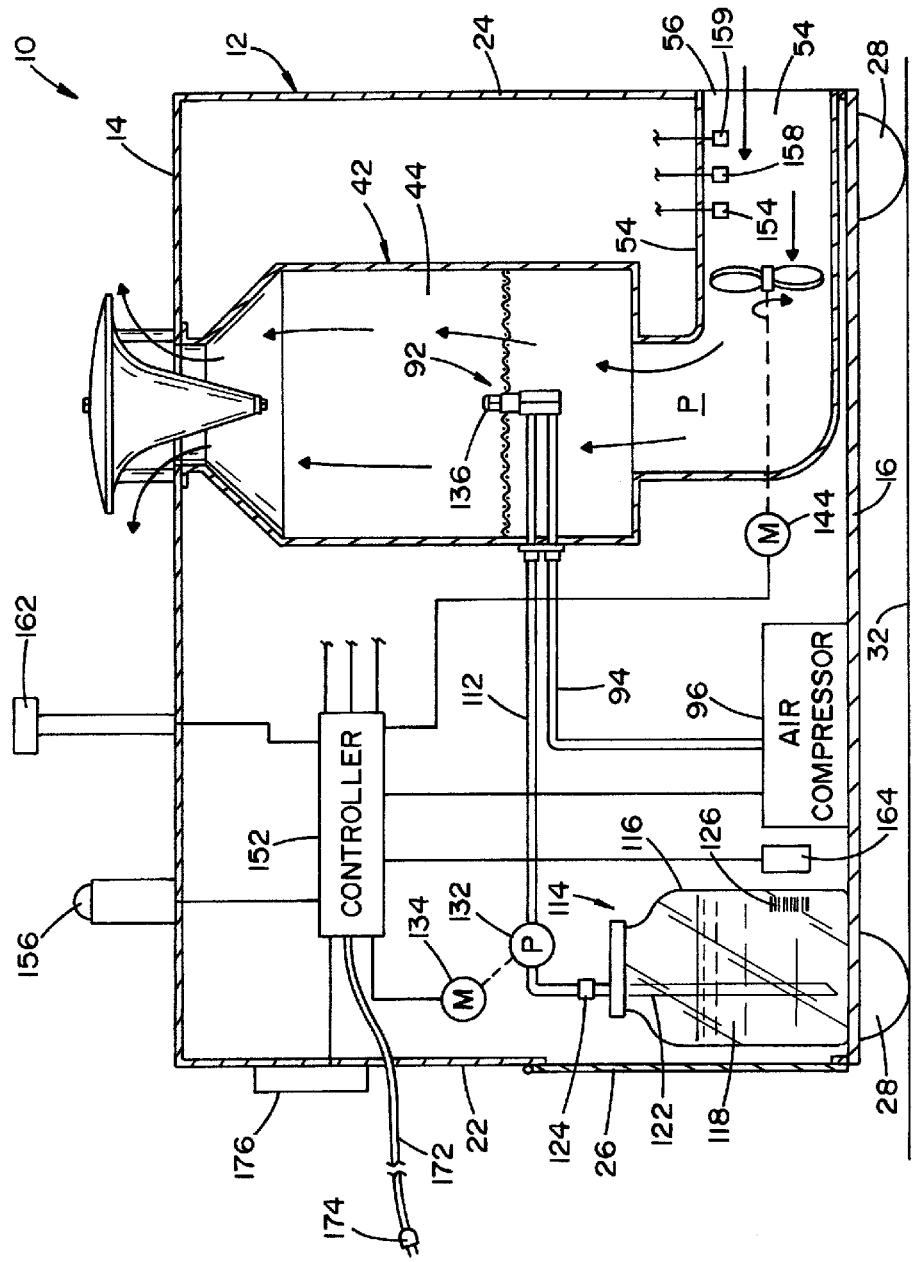

COLD-MIST DECONTAMINATION UNIT AND METHOD OF OPERATING SAME

FIELD OF THE INVENTION

The present invention relates generally to decontamination systems and, more particularly, to a decontamination system utilizing a cold mist to decontaminate a room or space.

BACKGROUND OF THE INVENTION

Decontamination methods are used in a broad range of applications and have used an equally broad range of sterilization agents. As used herein the term "decontamination" refers to processes, including, but not limited to, "deactivation of biocontamination," "deactivation of chemical contamination," "sterilization," "disinfection," and "sanitization." Chemicals used to effect decontamination are interchangeably referred to herein as decontaminants or sterilants.

In recent years, systems have been developed that utilize a cold mist of a sterilant or decontaminant to deactivate rooms or spaces. Cold-mist systems typically introduce an atomized decontaminant or sterilant into a room or space to effect the decontamination. Most of these systems tend to be simple and do not precondition the air within the room or space before introducing the atomized sterilant or decontaminant therein. Existing cold-mist decontamination systems usually introduce a given amount of sterilant into a room or space based upon the volume of the room or space and do not take into account the capacity of the air within the room or space to hold the sterilant. In this respect, the amount of sterilant a room or space can hold without the sterilant condensing on surfaces within the room or space is a function of the temperature and the initial humidity level within the room or space. One problem with such a system, particularly if it utilizes atomized hydrogen peroxide, is that water has a higher vapor pressure than hydrogen peroxide. As a result, atomized water droplets will vaporize, i.e., evaporate, more quickly in a room or space than will atomized hydrogen peroxide droplets. Under certain conditions, liquid hydrogen peroxide having a 5% concentration of hydrogen peroxide can produce liquid droplets within the room or space having a hydrogen peroxide concentration of 38%, which is very corrosive and highly flammable.

The present invention provides a cold-mist hydrogen peroxide decontamination system that optimizes a decontamination cycle by evaluating the environmental conditions within a room or space and introducing an atomized hydrogen peroxide mist into the room or space at a level that will not condense on objects within the room or space.

SUMMARY OF THE INVENTION

In accordance with a preferred embodiment of the present invention, there is provided a method of decontaminating a room or space, comprising the steps of:

a) providing a cold-mist decontamination device capable of generating an atomized mist comprised of a decontaminant and water from a liquid decontamination solution having a known concentration of the decontaminant therein, the decontamination system having an internal processor controlling the operation of the decontamination device;

b) inputting into the internal processor the parameters of the room or space and the concentration of the decontaminant in the decontamination solution;

c) measuring the temperature and humidity in the room or space;

d) determining the maximum amount of the decontamination solution that can be introduced into the room or space in atomized form without condensing the decontaminant on surfaces within the room or space and determining the actual amount of decontaminant in the maximum amount of decontamination solution;

e) determining a time period necessary to effect a predetermined level of decontamination in the room or space based upon the actual amount of decontaminant that can be introduced into the room or space based upon empirical data stored within the controller;

f) operating the decontamination unit to introduce an atomized mist of the decontamination solution into the room or space;

g) terminating the production of the atomized mist of the decontamination solution once the maximum amount has been introduced into the room or space; and h) providing an indication when the time period has elapsed as measured from the time production of the atomized mist had ceased.

An advantage of the present invention is a decontamination unit for generating a cold atomized mist of a hydrogen peroxide/water solution for decontaminating a room or space.

Another advantage of the present invention is a decontamination unit as described above that determines the maximum amount of a hydrogen peroxide/water solution that can be introduced into a room or space without condensing hydrogen peroxide on objects therein.

A still further advantage of the present invention is a decontamination unit described above that determines an exposure time based upon the maximum amount of hydrogen peroxide that can be introduced into a room or space.

Another advantage of the present invention is a decontamination unit described above that can sterilize, sanitize, or disinfect a room or space.

A still further advantage of the present invention is a decontamination unit described above that can calculate the maximum amount of hydrogen peroxide that can be introduced into a room or space without condensing hydrogen peroxide on objects therein based upon parameters of the room or space, conditions within the room or space, and whether a sterilization, sanitization, or disinfecting procedure is to be performed.

A still further advantage of the present invention is a decontamination unit described above that can detect the lowest temperature within a room or space and can calculate a maximum amount of hydrogen peroxide in the form of an atomized cold mist that can be introduced into the room or space without the hydrogen peroxide condensing on objects therein.

A still further advantage of the present invention is a decontamination unit described above wherein the unit can detect the concentration of hydrogen peroxide within the hydrogen peroxide/water solution by means of a scanning code on a container of the hydrogen peroxide/water solution.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 1 is a partially sectioned elevational view schematically illustrating a decontamination unit for decontaminating a room or space with an atomized, cold mist of hydrogen peroxide and water, illustrating a preferred embodiment of the present invention.

DETAILED DESCRIPTION OF PREFERRED EMBODIMENT

Referring now to the drawing wherein the showing is for the purpose of illustrating a preferred embodiment of the invention only and not for the purpose of limiting same, FIG. 1 shows a decontamination device 10, illustrating a preferred embodiment of the present invention. Decontamination device 10 is designed to decontaminate a room or space utilizing a cold mist sterilant. As used herein, the term decontamination refers to sterilization, disinfection, or sanitization.

Sterilization refers to a process or method that renders a product free of all forms of viable microorganisms.

Disinfection refers to a process or method that destroys disease-causing pathogens or other harmful microorganisms but might not kill bacterial spores.

Sanitization refers to a process or method that reduces bacteria by at least 99.9%.

In the embodiment shown, decontamination device 10 is comprised of an outer housing 12 that is generally rectangular in shape. Outer housing 12 includes a top wall 14, a bottom wall 16, and opposing side walls 22, 24. A panel 26 is formed in side wall 22 to allow access to the interior of outer housing 12. Wheels or casters 28 are provided beneath bottom wall 16 to allow decontamination device 10 to be easily portable along a floor surface, designated 32 in FIG. 1. An inner housing 42, disposed within outer housing 12, defines a mist-generating chamber 44. In the embodiment shown, mist-generating chamber 44 is generally cylindrical in shape and includes an open upper end 46 that is attached to top wall 14 of outer housing 12 and defines an opening 48 through top wall 14 of outer housing 12. A duct 52 is connected to the lower end of inner housing 42. Duct 52 defines an inner passageway 54 that communicates with misting chamber 44 through an opening in a bottom of inner housing 42. Passageway 54, defined by duct 52, communicates with the exterior of outer housing 12 through an opening 56 in side wall 24. In this respect, a path "P" is defined through outer housing 12 via passageway 54 through duct 52 and through misting chamber 44 defined by inner housing 42. Upper end 46 of inner housing 42 is formed to have an outwardly extending flange or collar portion 62 that defines annular surface 64.

A misting device 92 is provided within mist-generating chamber 44. An air line 94 connects misting device 92 to an air compressor 96 that is disposed within outer housing 12. A decontaminant line 112 connects misting device 92 to a source 114 of decontaminant. In the embodiment shown, source 114 of decontaminant is a container 116 containing a liquid decontamination solution 118. A siphoning tube 122 extends into liquid decontamination solution 118 within container 116. Siphoning tube 122 is connected by a connector fitting 124 to decontaminant line 112. As will be described in greater detail below, container 116 is identified by a bar code 126. In the embodiment shown, a bar code is provided on container 116. Bar code 126 provides coded information regarding the composition and concentration of decontamination solution 118 held in container 116. In a preferred embodiment, decontamination solution 118 is a hydrogen peroxide and water solution.

A metering pump 132 is disposed within decontaminant line 112 to meter predetermined amounts of decontamination solution 118 from container 116 to misting device 92. A pump motor 134 drives metering pump 132. In the embodiment shown, misting device 92 is comprised of a conventional nozzle 136 capable of creating a mist when liquid decontamination solution 118 pumped by pump 132 from container 116 is combined with compressed air from air compressor 96.

A blower fan 142 is provided within passageway 54 to convey air from outside outer housing 12 through mist-generating chamber 44. A fan motor 144 is connected to blower fan 142 to drive the same.

A controller 152 is provided to control the operations of metering pump motor 134 and fan motor 144. A temperature sensor 154, an infrared temperature sensor 156, a humidity sensor 158, a hydrogen peroxide sensor 159 and a directional laser sensor 162 are provided to determine certain parameters within the room or space to be decontaminated. Temperature sensor 154 is connected to controller 152 and is operable to provide signals to controller 152 indicative of the temperature within the room or space surrounding decontamination device 10. Infrared sensor 156 is connected to controller 152 and is operable to provide signals indicative of the temperature in different regions of the room or space. In this respect, infrared sensor 156 is capable of detecting cold areas or pockets within a room or space. Humidity sensor 158 is connected to controller 152 and provides signals indicative of the humidity within the room or space to be decontaminated. Hydrogen peroxide sensor 159 is connected to controller 152 and is operable to provide signals to controller 152 indicative of the level of hydrogen peroxide in the room or space. Laser sensor 162 is connected to controller 152 and is operable to provide signals indicative of dimensions of the room or space within which the decontamination device 10 is located. A sensor 164 is also provided to read bar code 126 on decontaminant container 116. As indicated above, bar code 126 is provided on decontaminant container 116 to provide information regarding decontamination solution 118 within container 116. Accordingly, sensor 164 is positioned adjacent to the storage location for decontaminant container 116 to provide signals to controller 152 indicative of the contents of decontaminant container 116. A power cable 172, connected at one end to controller 152, extends through side wall 22 of outer housing 12. Power cable 172 includes a conventional plug 174 at the free end thereof to connect to standard electrical outlets within the room or space to be decontaminated to provide operation power to decontamination device 10. As will be appreciated, decontamination device 10 may contain an internal power source, such as a battery to provide operation power to the various components contained therein. An input display panel 176 is provided on the exterior of side wall 22 of outer housing 12. Input display panel 176 is connected to controller 152 and allows users of decontamination device 10 to input information into controller 152. Input display panel 176 may also display information concerning the operation of decontamination device 10, such as operating conditions.

A method of operating decontamination device 10 shall now be described. Prior to performing a decontamination procedure, container 116 containing a decontamination solution 118 is inserted into decontamination device 10 through access panel 26 in side wall 22 of decontamination device 10. In accordance with one aspect of the present invention, decontamination solution 118 may be a sterilizing solution, a disinfecting solution, or a sanitizing solution. In this respect, each type of solution has a specific identification bar code 126 associated therewith applied to container 116 to identify the type of solution contained within container 116. In addition to identifying the type of active ingredient in the decontamination solution 118, the bar code 126 on container 116 also identifies the concentration of the active ingredient within decontamination solution 118.

Container 116 is placed within outer housing 12 such that bar code 126 on container 116 is positioned in proximity to sensor 164 wherein bar code 126 on container 116 can be scanned and read by sensor 164. Based on signals provided by sensor 164, controller 152 can identify the contents of container 116, specifically, the type of active ingredient (the decontaminant), i.e., a sterilant, a disinfectant, or a sanitizer, as well as the concentration of the decontaminant within decontamination solution 118 in container 116. As will be described in greater detail below, controller 152 is programmed to operate in three modes, namely, a sterilization mode, a disinfection mode, or a sanitization mode. By identifying the contents of container 116, controller 152 is able to confirm that the appropriate decontamination solution 118 is present within decontamination device 10 so as to perform a desired decontamination operation.

During operation of decontamination device 10, liquid decontamination solution 118 is metered to misting device 92 by operation of metering pump motor 134. Controller 152 controls the operating speed of pump motor 134 to control the amount of decontamination solution 118 introduced into misting device 92 positioned in mist-generating chamber 44. Decontamination solution 118 is introduced into a stream of compressed air that is introduced into misting device 92 by air compressor 96 through air line 94. Introduction of liquid decontamination solution 118 and compressed air into misting nozzle 136 on misting device 92 creates an atomized mist of the decontamination solution 118 in mist-generating chamber 44. At the same time that misting device 92 is creating a mist, controller 152 operates fan motor 144 to cause blower fan 142 to convey external air into and through passageway 54 of duct 52 and into and through mist-generating chamber 44. Air flowing through the mist-generating chamber 44 collects the atomized decontaminant mist and injects it into the room or space.

In accordance with one aspect of the present invention, controller 152 is programmed to control operation of metering pump motor 134 and fan motor 144 to introduce a predetermined amount of decontaminant into the room or space in the form of an atomized mist. The amount of decontaminant introduced into the room or space is based upon the parameters of the room or space as well as the conditions within the room or space, namely, the temperature and humidity within the room or space.

In accordance with the present invention, controller 152 is programmed to operate decontamination device 10 so as to introduce a desired amount of liquid decontamination solution 118 as an atomized mist into the room or space based upon the type of decontamination procedure selected. In this respect, controller 152 is programmed to operate in three modes: a sterilization mode, a disinfection mode, or a sanitization mode. One of these three modes of operation is selected by the user using input display pad 176. Once an operating mode has been selected, controller 152 determines certain parameters regarding the room or space. Parameters regarding the temperature, humidity, and size of the room or space may be inputted using input display panel 176. Alternately, this information can be determined using sensors 154, 156, 158, 162 that form part of decontamination device 10. In this respect, temperature sensor 154 provides an indication as to the temperature within the room or space. Humidity sensor 158 provides information to controller 152 regarding the humidity level within the room or space. Directional laser sensor 162 may provide an indication as to the parameters of the room or space, namely, the distance between the walls and the ceiling and the floor to provide a volume within the room or space. Cold spots, regions or areas within the room or space can be determined using infrared sensor 156. In this respect, as will be appreciated from a further reading of the present specification, calculations regarding the amount of decontaminant that may be introduced into the room or space are determined based upon the coldest regions within the room or space where condensation of the liquid sterilant on surfaces in the room or space is most likely to occur. Controller 152 also determines the actual amount of active decontaminant within the decontaminant solution 118. This information can be inputted into the decontamination device 10 using the input display panel 176, or sensor 164 disposed adjacent to container 116 can determine the contents of container 116 based upon bar code 126 that identifies the contents of container 116. Knowing the parameters of the room or space, as well as the temperature and relative humidity characteristics within the room or space, and further knowing the actual amount of active decontaminant, i.e., sterilant, disinfectant, or sanitizer, within decontaminant solution 118, controller 152 determines the maximum amount of decontamination solution 118 that can be introduced into the room or space without causing condensation of decontamination solution 118 onto surfaces within the room or space. This determination of maximum amount of the decontamination solution 118 that can be introduced into the room or space is based upon empirical data stored within the memory of controller 152.

Having determined the maximum amount of decontamination solution 118 that can be introduced into the room or space, controller 152 determines the time necessary to effect the level of decontamination selected, namely, sterilization, disinfection, or sanitization, based upon the actual amount of the sterilant, disinfectant, or sanitizer that can be introduced into the room or space. Controller 152 then initiates operation of decontamination device 10 to introduce the atomized mist of decontamination solution 118 into the room or space. Operation of decontamination device 10 ceases once the maximum amount of decontamination solution 118 has been introduced into the room or space. Once the production of atomized mist has ceased and the required time to decontaminate the room or space has passed, controller 152 provides an indication that the predetermined exposure time limit necessary to effect the desired level of decontamination has been completed. At this point, controller 152 may be connected to a destroyer device to initiate operation of a destroyer unit (not shown) to destroy any sterilant vapors or disinfectant vapors that may still be present in the room or space. In the alternative, controller 152 may be programmed to determine a "dissipation period." The dissipation period is the time within which vapors in the room or space would dissipate or be destroyed. Thereafter, controller 152 can provide an indication that the room or space is safe to occupy by humans.

The present invention incorporates a feedback control system. Feedback control will allow the controller to calculate the dew point on the room based on temperature, relative humidity and hydrogen peroxide concentration. To prevent condensation on the coldest surface, the lowest temperature is measured with the infrared sensor 156. The dew point is measured with the temperature sensor in the return air flow. The control is programmed with the "D" valve which considers hydrogen peroxide and water levels (concentration and saturation) to determine contact time.

The present invention thus provides a simple decontamination and a method of using the same for automatically sterilizing, disinfecting, or sanitizing a room or region.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A method of decontaminating a room or space, comprising the steps of:
   a) providing a cold-mist decontamination device capable of generating an atomized mist comprised of a decontaminant and water, from a liquid decontamination solution having a known concentration of said decontaminant therein, said decontamination system having an internal processor controlling the operation of said decontamination device, wherein the concentration of decontaminant in said decontamination solution is inputted into said internal processor by a sensor identifying the decontaminant and the concentration of the decontaminant from a digital code on a container that contains said decontamination solution;
   b) inputting into said internal processor the parameters of said room or space and the concentration of the decontaminant in said decontamination solution;
   c) measuring the temperature and humidity in said room or space;
   d) determining the maximum amount of said decontamination solution that can be introduced into said room or space in atomized form without condensing said decontaminant on surfaces within said room or space and determining the actual amount of decontaminant in said maximum amount of decontamination solution;
   e) determining a time period necessary to effect a predetermined level of decontamination in said room or space based upon the actual amount of decontaminant that can be introduced into said room or space based upon empirical data stored within said controller;
   f) operating said decontamination unit to introduce an atomized mist of said decontamination solution into said room or space;
   g) terminating the production of the atomized mist of the decontamination solution once the maximum amount has been introduced into said room or space; and
   h) providing an indication when said time period has elapsed as measured from the time production of the atomized mist had ceased.

2. A method of decontaminating a room or space as defined in claim 1, wherein said decontaminant is hydrogen peroxide.

3. A method of decontaminating a room or space as defined in claim 1, wherein the concentration of decontaminant in said decontamination solution is inputted into said internal processor by an operator.

4. A method of decontaminating a room or space as defined in claim 1, wherein the parameters of said room or space are inputted into said controller by sensors detecting the parameter of said room or space.

5. A method of decontaminating a room or space as defined in claim 1, wherein the parameters of said room or space are inputted into said controller by an operator.

6. A method of decontaminating a room or space as defined in claim 1, wherein said decontaminant is a sterilant.

7. A method of decontaminating a room or space as defined in claim 1, wherein said decontaminant is disinfectant.

8. A method of decontaminating a room or space as defined in claim 1, wherein said decontaminant is a sanitizer.

9. A method of decontaminating a room or space as defined in claim 1, wherein said temperature inputted into said internal processor is the lowest temperature in said room or space.

10. A method of decontaminating a room or space as defined in claim 9, wherein said lowest temperature in said room is determined by an infrared sensor.

11. A method of decontaminating a room or space as defined in claim 1, further comprising:
   i) destroying any vapors of atomizing mist present in said room or space.

12. A method of decontaminating a room or space as defined in claim 1, further comprising:
   j) determining a dissipation period within which vapors in said room or space would dissipate; and
   k) providing an indication that the room or space is safe to occupy by humans.

13. A method of decontaminating a room or space, comprising:
   a) providing a decontamination system that includes a decontamination device and a processor that controls the operation of the decontamination device;
   determining a volume of the room or space to be decontaminated, a temperature and a humidity within the room or space;
   c) determining a concentration of a sterilant in an aqueous sterilant solution by placing a container of the aqueous sterilant solution into the decontamination system such that a bar code positioned on the container is read by a bar code reader located within the decontamination system, the concentration of the sterilant in the aqueous sterilant solution encoded within the bar code;
   inputting the information obtained in steps (b) and (c) into the processor, the processor, using the information inputted therein, calculating a maximum amount of sterilant that may be introduced into the room or space in an atomized mist form such that the sterilant does not condense on any objects located within the room or space;
   e) operating the decontamination system such that the decontamination device introduces the atomized mist of the aqueous sterilant solution into the room or space;
   f) terminating the production of the atomized mist of the aqueous sterilant solution once the maximum amount of sterilant has been introduced into the room or space; and
   g) exposing the objects in the room or space to the atomized mist for a period of time sufficient to decontaminate the objects located within the room or space.

* * * * *